US009504383B2

(12) United States Patent
Seassau et al.

(10) Patent No.: US 9,504,383 B2
(45) Date of Patent: Nov. 29, 2016

(54) DETECTION OF AN OCULOMOTOR ABNORMALITY IN A PATIENT BY MEANS OF A VISUAL SEARCH TEST

(75) Inventors: Magali Seassau, Paris (FR); Serge Kinkingnehun, Virty sur Seine (FR)

(73) Assignee: E(YE)BRAIN, Ivry sur Seine (FR)

( * ) Notice: Subject to any disclaimer, the term of this patent is extended or adjusted under 35 U.S.C. 154(b) by 319 days.

(21) Appl. No.: 14/236,650

(22) PCT Filed: Aug. 10, 2012

(86) PCT No.: PCT/FR2012/051881
§ 371 (c)(1), (2), (4) Date: Apr. 15, 2014

(87) PCT Pub. No.: WO2013/021144
PCT Pub. Date: Feb. 14, 2013

(65) Prior Publication Data
US 2014/0228704 A1 Aug. 14, 2014

(30) Foreign Application Priority Data
Aug. 11, 2011 (FR) ..................................... 11 57308

(51) Int. Cl.
*A61B 5/00* (2006.01)
*A61B 3/113* (2006.01)
*A61B 5/16* (2006.01)
*A61B 3/08* (2006.01)
*A61B 3/028* (2006.01)

(52) U.S. Cl.
CPC ................ *A61B 3/113* (2013.01); *A61B 5/16* (2013.01); *A61B 3/028* (2013.01); *A61B 3/085* (2013.01)

(58) Field of Classification Search
CPC ........ A61B 3/00; A61B 3/028; A61B 3/032; A61B 3/08; A61B 3/085; A61B 5/16
See application file for complete search history.

(56) References Cited

U.S. PATENT DOCUMENTS 5,309,185 A * 5/1994 Harper ................... A61B 3/032 351/202
5,550,602 A * 8/1996 Braeuning ............. A61B 3/024 348/E13.033
7,071,831 B2 * 7/2006 Johns ..................... A61B 3/113 340/575
8,240,851 B2 * 8/2012 Reichow .................. A61B 3/18 351/203
8,513,055 B2 * 8/2013 Reichow ................ A61B 3/032 351/203
8,808,195 B2 * 8/2014 Tseng ..................... A61B 3/113 600/558

OTHER PUBLICATIONS

International Search Report dated Dec. 11, 2012, corresponding to PCT/FR2012/051881.
J.W. Bruce Evans, et al.; "Investigation of Accommodative and Binocular Function in Dyslexia"; vol. 14, No. 1; Jan. 1, 1994; pp. 5-19.
Stephanie Jainta, et al.; Dyslexic Children Are Confronted with Unstable Binocular Fixation While Reading; Apr. 6, 2011; pp. 1-9.
Yang Qing, et al.; Binocular Coordination of Saccades at Far and at Near in Children and Adults; vol. 3; Oct. 2, 2003; pp. 554-561.
G.F. Eden, et al.; Differences in Eye Movements and Reading Problems in Dyslexic and Normal Children; vol. 34, No. 10; May 1, 1994; pp. 1345-1358.
H.I. Blythe, et al.; The Binocular Coordination of Eye Movements During Reading in Children and Adults; vol. 46, No. 22; Oct. 1, 2006; pp. 3898-3908.
Prado, et al.; "The Eye Movements of Dyslexic Children During Reading and Visual Search: Impact of the Visual Attention Span"; vol. 47, No. 19; Sep. 1, 2007; pp. 2521-2530.

* cited by examiner

*Primary Examiner* — Max Hindenburg
(74) *Attorney, Agent, or Firm* — Young & Thompson

(57) ABSTRACT

The visual search test makes it possible to establish a parameter for binocular coordination that is useful for detecting an oculomotor abnormality, in particular in the context of detecting dyslexia. A system for assisting in the detection is also described.

18 Claims, 5 Drawing Sheets

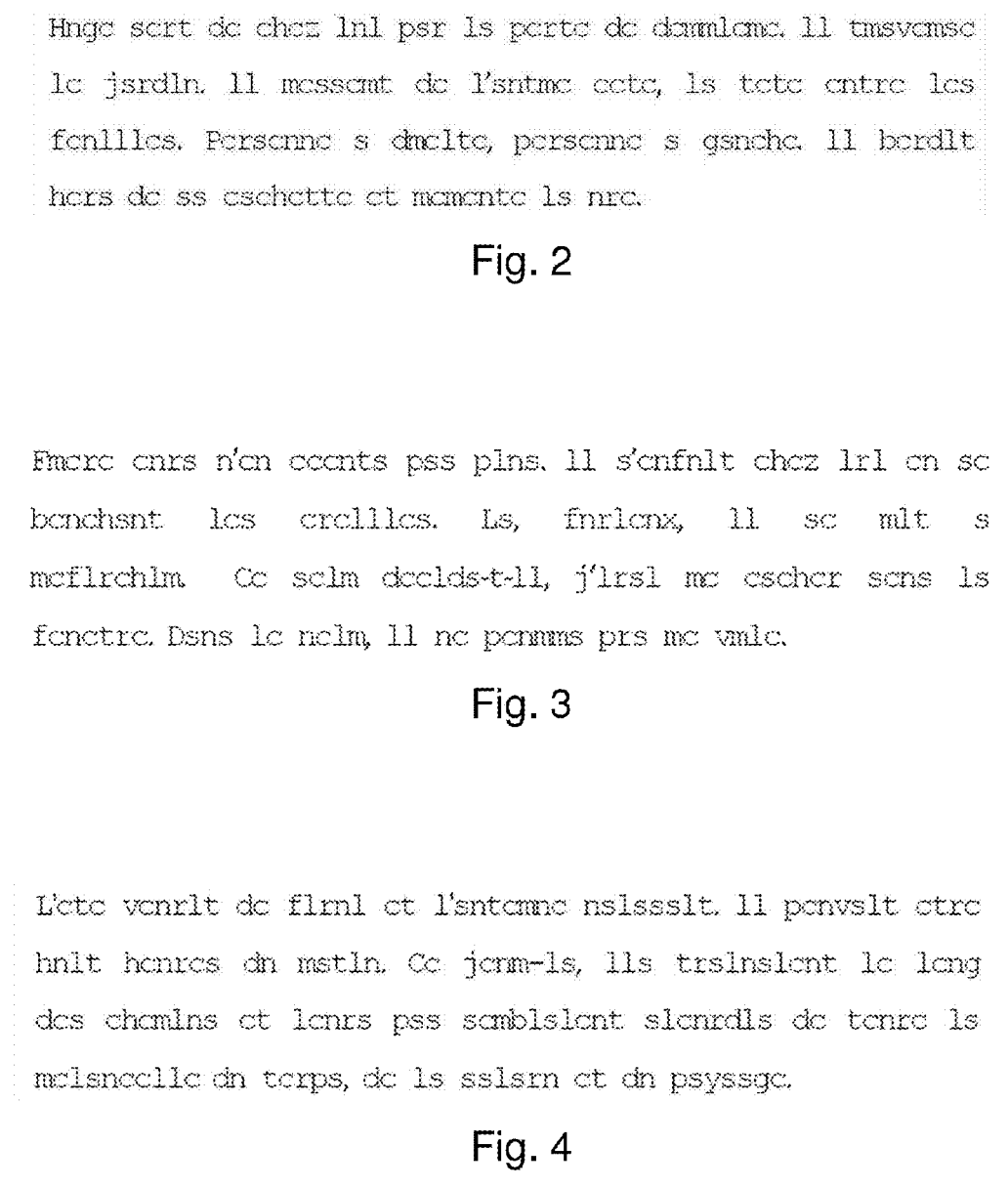

Hngc scrt dc chcz lnl psr ls pcrtc dc dcmmlcmc. ll tmsvcmsc lc jsrdln. ll mcsscmt dc l'sntmc cctc, ls tctc cntrc lcs fcnlllcs. Pcrscnnc s dmcltc, pcrscnnc s gsnchc. ll bcrdlt hcrs dc ss cschcttc ct mcmcntc ls nrc.

Fig. 2

Fmcrc cnrs n'cn cccnts pss plns. ll s'cnfnlt chcz lrl cn sc bcnchsnt lcs crclllcs. Ls, fnrlcnx, ll sc mlt s mcflrchlm. Cc sclm dcclds-t-ll, j'lrsl mc cschcr scns ls fcnctrc. Dsns lc nclm, ll nc pcnmms prs mc vmlc.

Fig. 3

L'ctc vcnrlt dc flrnl ct l'sntcmnc nslssslt. ll pcnvslt ctrc hnlt hcnrcs dn mstln. Cc jcnm-ls, lls trslnslcnt lc lcng dcs chcmlns ct lcnrs pss scmblslcnt slcnrdls dc tcnrc ls mclsnccllc dn tcrps, dc ls sslsrn ct dn psyssgc.

Fig. 4

| Subject | $C_{Sacc}$ | $D_{Sacc}$ | $C_{Fix}$ | $D_{Fix}$ | $T_{Fix}$ |
|---|---|---|---|---|---|
| D1 | 2,95 | 1,05 | 1,60 | 2,29 | 641,33 |
| D2 | 3,35 | 1,89 | 1,16 | 1,81 | 676,33 |
| D3 | 3,11 | 0,35 | 1,07 | 0,37 | 570,88 |
| D4 | 3,76 | 0,69 | 1,62 | 1,06 | 708,64 |
| D5 | 4,11 | 1,57 | 0,92 | 1,21 | 489,28 |
| ND1 | 3,16 | 0,21 | 0,38 | 0,23 | 365,42 |
| ND2 | 3,40 | 0,20 | 0,40 | 0,19 | 321,32 |
| ND3 | 3,26 | 0,24 | 0,92 | 0,36 | 421,95 |
| ND4 | 2,93 | 0,32 | 0,83 | 0,35 | 440,25 |
| *Normal range for healthy subjects* | ***3,27*** | ***0,35*** | ***0,78*** | ***0,34*** | ***419,68*** |
| *Upper threshold* | ***4,89*** | ***0,77*** | ***1,25*** | ***0,54*** | ***541,00*** |

Fig. 7

| Subject | $C_{Sacc}$ | $D_{Sacc}$ | $C_{Fix}$ | $D_{Fix}$ | $T_{Fix}$ |
|---|---|---|---|---|---|
| D1 | 3,75 | 1,68 | 1,21 | 1,57 | 474,51 |
| D2 | 2,69 | 0,88 | 1,48 | 0,67 | 914,12 |
| D3 | 3,92 | 0,53 | 1,04 | 0,57 | 534,57 |
| D4 | 2,80 | 0,81 | 1,04 | 0,78 | 433,50 |
| D5 | 3,29 | 0,89 | 1,27 | 0,55 | 529,11 |
| D6 | 2,91 | 0,86 | 2,24 | 1,80 | 522,66 |
| D7 | 3,21 | 0,77 | 1,12 | 1,15 | 475,69 |
| D8 | 3,70 | 1,61 | 2,03 | 1,69 | 532,62 |
| D9 | 4,05 | 1,21 | 0,88 | 0,61 | 363,55 |
| D10 | 3,13 | 0,92 | 0,86 | 0,56 | 408,06 |
| D11 | 6,65 | 0,72 | 2,01 | 0,85 | 482,92 |
| ND1 | 4,61 | 0,52 | 1,10 | 0,42 | 456,74 |
| ND2 | 2,49 | 0,18 | 0,56 | 0,19 | 328,82 |
| ND3 | 3,44 | 0,34 | 0,38 | 0,34 | 452,07 |
| ND4 | 3,12 | 0,22 | 0,53 | 0,20 | 347,67 |
| *Normal range for healthy subjects* | ***3,24*** | ***0,36*** | ***0,73*** | ***0,32*** | ***420,62*** |
| *Upper threshold* | ***4,67*** | ***0,81*** | ***1,28*** | ***0,51*** | ***516,10*** |

Fig. 8

| ***Subject*** | $C_{Sacc}$ | $D_{Sacc}$ | $C_{Fix}$ | $D_{Fix}$ | $T_{Fix}$ |
|---|---|---|---|---|---|
| D1 | 3,54 | **1,26** | **1,32** | **0,94** | **672,16** |
| D2 | 4,17 | 0,24 | **2,07** | 0,40 | **549,77** |
| D3 | **5,46** | **6,36** | **3,76** | **5,35** | **549,89** |
| ND1 | 3,88 | 0,29 | 0,53 | 0,36 | 348,28 |
| ND2 | 2,18 | 0,33 | 0,49 | 0,26 | 304,38 |
| ND3 | 2,24 | 0,26 | 0,64 | 0,28 | 373,86 |
| ND4 | 2,68 | 0,48 | 0,64 | 0,46 | 394,15 |
| *Normal range for healthy subjects* | ***3,00*** | ***0,38*** | ***0,53*** | ***0,33*** | ***364,81*** |
| *Upper threshold* | ***4,49*** | ***0,70*** | ***0,95*** | ***0,51*** | ***465,90*** |

Fig. 9

DETECTION OF AN OCULOMOTOR ABNORMALITY IN A PATIENT BY MEANS OF A VISUAL SEARCH TEST

The present invention relates to a method for detecting an oculomotor abnormality in a subject, which can be at the origin of dyslexia, as well as a system for assisting said detection.

Oculomotor disorder, i.e. an abnormality of the movement of the eyes, may be manifested in certain diseases, for example strabismus or surface dyslexia, which is one of the main types of dyslexia, another main type of dyslexia being phonological dyslexia, in which a subject confuses letters or sounds.

Surface dyslexia can incorporate dyspraxia of gaze, i.e. poor binocular coordination in a subject. Binocular coordination reflects the right-left coordination between the subject's two eyes. In other words, the relative movement of the two eyes during one and the same task is involved, otherwise called "vergence" in the literature, introducing, in the case of dyspraxia, a spatial divergence between the two eyes that can be measured in degrees.

The publications "Dyslexic children are confronted with unstable binocular fixation while reading" (S. Jainta et al., 2011) (see page 1, right-hand column, lines 3 to 15) and "The binocular coordination of eye movements during reading in children and adults", H. Blythe et al., 2006 (see section 1.1 and p. 3899, right-hand column, lines 49 to 55) employ an analysis of this binocular coordination during reading tests.

Numerous tests have been introduced with the intention of detecting surface dyslexia in young children as early as possible.

The works of Rayner (1978) and Pavlidis (1981) in particular showed that children with such dyslexia had serious reading problems, in particular characterized by a large number of regressive fixations (i.e. towards the left for a text reading from left to right, as opposed to progressive fixations), shorter saccades (saccades representing movement of the eyes from one word to another) and longer fixations than normal readers of the same age.

Reading tests have thus been developed, as mentioned in these two aforementioned publications, and exploitation of parameters has been refined. A drawback of reading tests is that they require the subjects to have the ability to read. Therefore they do not promote the detection of oculomotor abnormalities in very young subjects, generally under 7 years of age.

In the work "The eye movements of dyslexic children during reading and visual search: Impact of the visual attention span" by C. Prado, M. Dubois and S. Valdois (Vision Research 47 pp. 2521-2530, 2007), a reading test of text in French and a visual search test for a letter within a paragraph lacking semantic content were performed on child subjects in order to determine the influence of certain parameters in the detection of dyslexia. The total number of fixations, the average duration of fixation, the percentage and duration of regressive fixations, and the number and duration of progressive fixations were calculated based on recordings of the movements of the subjects' right eye.

This work comes to one conclusion, in agreement with other earlier reports (see in particular "Reading Text Increases Binocular Disparity in Dyslexic Children" by J. Kirkby et al., 2011, and "Perhaps correlational but not causal: No effect of dyslexic readers' magnocellular system on their eye movements during reading" by F. Hutzler et al., 2006), according to which there would be no difference in the profile of movement of the eyes between dyslexic subjects and healthy subjects, i.e. no difference of binocular coordination between these subjects, during a visual search test, in contrast to a far more significant reading test.

However, contrary to this assumption, the inventors have found that the use of one or more well-chosen parameters makes it possible to identify dyslexic subjects by a visual search test.

In this context, the invention relates more particularly to a visual search test for establishing a parameter of binocular coordination in a subject, comprising the following steps:

- subjecting the subject to a visual search task for occurrences of a symbol within a succession of symbols;
- during said task, recording, preferably independently and simultaneously, the movements of the subject's two eyes using a device for tracking eye movements; then
- determining, using a digital processing device, the value of at least one parameter of binocular coordination from the recordings obtained.

It should be pointed out that the binocular coordination parameters measured by the visual search test of the invention are not sufficient in themselves to make a diagnosis of dyslexia and that other elements or clinical data must be taken into account to reach the conclusion that the subject suffers from an oculomotor disorder that may lead to dyslexia. It should in fact be pointed out that an oculomotor abnormality, in itself, is not generally regarded as a disorder or a pathology.

Such a test therefore makes it possible to obtain one or more parameters of binocular coordination, which, in combination with other factors, parameters or clinical data, can be of assistance in screening for dyslexia.

Thus, in an extension of the invention, the visual search test according to the invention can be used in a method for detecting an oculomotor abnormality in a subject, in which, for example:

- the subject is set a visual search task for occurrences of a symbol within a succession of symbols;
- during said task, the movements of the subject's two eyes are recorded, preferably independently and simultaneously, using a device for tracking eye movements;
- using a digital processing device, the value of at least one parameter of binocular coordination is determined from the recordings;
- the value determined is compared with at least one threshold value in order to determine an oculomotor abnormality.

This method of detection, in contrast to current knowledge, allows better identification of subjects who have an oculomotor abnormality, for example as a cause of dyslexia or strabismus, by the use of a visual search test according to the invention.

Thanks to the invention, disorders or diseases such as surface dyslexia can henceforth be detected early in child subjects. In fact, the visual search test does not require reading ability, as is the case with many tests for detecting dyslexia. Moreover, a succession of symbols, even if these symbols can take the form of letters, has the particular feature that it lacks semantic content. This has the advantage of limiting the syllabic associations that a reader would be tempted to make and which could interfere with the visual search.

The effectiveness of the invention is based on the use of at least one parameter of binocular coordination. In fact, the inventors have found that such a parameter, in particular of the disconjugacy type as mentioned later, varies significantly between a healthy subject and a dyslexic subject.

Said parameter of binocular coordination can be obtained by processing the recordings of the movements of the two eyes measured during the test or else subsequently, in the absence of the subject, from measurements taken previously.

Correlatively, the invention relates to a system for assisting the detection of an oculomotor abnormality in a subject by a visual search test, comprising:

- a testing module for setting the subject a visual search task for occurrences of a symbol within a succession of symbols;
- a module for tracking eye movements, configured for recording, during said task, the movements of the subject's two eyes;
- a digital processing module configured for determining the value of at least one parameter of binocular coordination from the recordings;
- a module for comparing the value determined with at least one threshold value so as to determine an oculomotor abnormality.

The device according to the invention offers advantages similar to those of the method described above, in particular of making it possible to detect an oculomotor disorder linked to dyslexia, by means of the visual search test. This system for assisting detection can be used for diagnosing dyslexia, in particular surface dyslexia.

Optional features of the invention are, moreover, defined in the dependent claims.

For example, a parameter of binocular coordination can comprise at least one parameter of binocular disconjugacy in amplitude.

Binocular disconjugacy in amplitude represents the difference in the amplitude of the measured movements between the two eyes.

The inventors have in fact found that, in many patients with dyslexia, the two eyes do not have the same behaviour during the different phases (saccade or fixation period) of the visual search test, which is not the case in healthy subjects.

Application of this parameter of disconjugacy, even taken in isolation, thus allows rapid identification of certain affected subjects.

Moreover, a parameter of binocular disconjugacy can comprise a parameter of disconjugacy during saccades representative of a difference in movement between the two eyes during displacement of said eyes from one symbol to another.

This parameter therefore quantifies the difference in amplitude in the movement of the two eyes during a saccade.

Symmetrically, a parameter of binocular disconjugacy can comprise a parameter of disconjugacy of post-saccadic fixation period representative of a difference in movement between the two eyes during the fixation of a symbol.

It is in this case a question of the difference in amplitude in the movement of the eyes during fixation of a symbol, typically a letter in a paragraph lacking semantic content.

The inventors have found that, in dyslexic subjects, the disconjugacy introduced during the saccade phase (the outer eye moving more quickly than the inner eye) is compensated by a disconjugacy during the fixation phase following the saccade. Such behaviour was found to be absent in healthy subjects.

Thus, preferably, these two parameters of disconjugacy will be combined in the detection of an oculomotor abnormality according to the invention.

In an embodiment of the invention, determination of the value of at least one parameter of binocular coordination comprises identification, by the digital processing device, of saccades and of post-saccadic fixations in the recordings, and comprises the calculation of the at least one parameter of binocular coordination as a function of the saccades and post-saccadic fixations identified.

As mentioned previously, the inventors in fact found that the binocular coordination of dyslexic subjects is altered for each of the phases of visual search, namely for the saccade and for post-saccadic fixation.

According to this embodiment, a parameter of binocular coordination can be representative of an average of several saccades or several post-saccadic fixations.

In an embodiment, the method according to the invention also comprises determination of at least one parameter of binocular conjugacy or coordination in amplitude from the recordings and comparison of the parameter of conjugate movement with at least one threshold value.

The binocular conjugacy in amplitude represents the average of the amplitude of the measured movements of the two eyes.

The inventors also found that certain parameters of binocular conjugate movement differ between dyslexic subjects and healthy subjects, but generally to a lesser extent than the parameters of binocular disconjugacy.

The parameters of binocular conjugacy in amplitude, for example the binocular conjugacy of post-saccadic fixation period, will therefore generally be combined with parameters of disconjugacy.

Furthermore, in a particular embodiment of the invention, the following parameters are determined from the recordings and compared with respective threshold values to determine an oculomotor abnormality:

- a parameter of disconjugacy during saccades in amplitude,
- a parameter of disconjugacy of post-saccadic fixation period in amplitude,
- a parameter of conjugacy of post-saccadic fixation period in amplitude,
- a duration of post-saccadic fixation period.

This combination appeared, in the eyes of the inventors, as effective in the detection of dyslexia in child subjects.

A main application of the invention is in fact the detection of dyslexia in child subjects, in particular surface dyslexia, in particular in young children not yet able to read.

Other features and advantages of the invention will become apparent from the following description, illustrated by the attached drawings, in which:

FIG. 2 shows an example of a paragraph for a visual search test suitable for children from 7 to 9 years;

FIG. 3 shows an example of a paragraph for a visual search test suitable for children from 10 to 12 years;

FIG. 4 shows another example of a paragraph for a visual search test suitable for children from 13 to 15 years;

FIG. 7 is a summary table of the results of the visual search test for a group of child subjects between 7 and 9 years;

FIG. 8 is a summary table of the results of the visual search test for a group of child subjects between 10 and 12 years; and FIG. 9 is a summary table of the results of the visual search test for a group of child subjects between 13 and 15 years.

Figure 1:
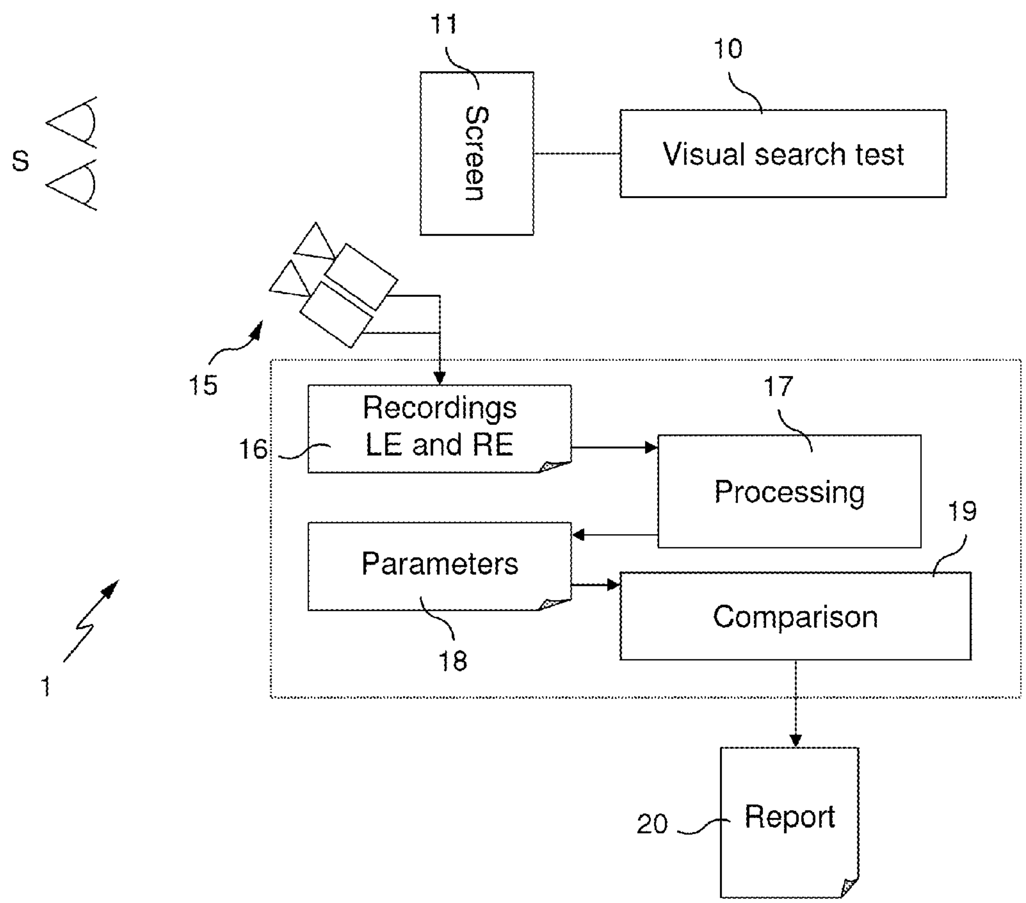
FIG. 1 shows schematically a system for assisting the detection of an oculomotor abnormality by a visual search test, according to the invention.

In the embodiment in FIG. 1, a system 1 for assisting the detection of an oculomotor abnormality according to the invention comprises a test part and an acquisition and processing part.

The test part in particular comprises a testing module 10 for setting the subject S a visual search task for occurrences of a symbol within a succession of symbols, as well as a screen 11 for displaying this succession of symbols to the subject at a distance between about 45 and 65 cm, preferably about 60 cm.

FIGS. 2 to 4 illustrate examples of paragraphs of consonants without semantic content that are presented to the subject.

In the experiments conducted and described below, this paragraph is displayed in a visual field of the subject S with a width of 29 degrees (horizontal coordinates not shown in FIGS. 5 and 6) and a height of 6.4 degrees.

The test module 10 instructs the subject S to look for the letters "r" in the paragraph displayed.

Returning to FIG. 1, the acquisition and processing part comprises a video acquisition module 15 placed opposite the subject's eyes for acquiring at a high rate (for example every 4 ms) the displacement of each eye during the visual search test.

The video acquisition module 15 carries out a pre-processing of the images acquired, according to the conventional techniques of image processing, in order to obtain a recording, over time, of the displacement of each eye in terms of amplitude on the horizontal axis (degrees relative to the centre of vision).

The video acquisition module 15 tracks the eye movements for both eyes simultaneously. The Mobile Eyebrain Tracker (Mobile EBT®) system can be used for this purpose.

The two curves obtained 16 are then recorded in the system for immediate or later processing on collection of the data.

Figure 5:
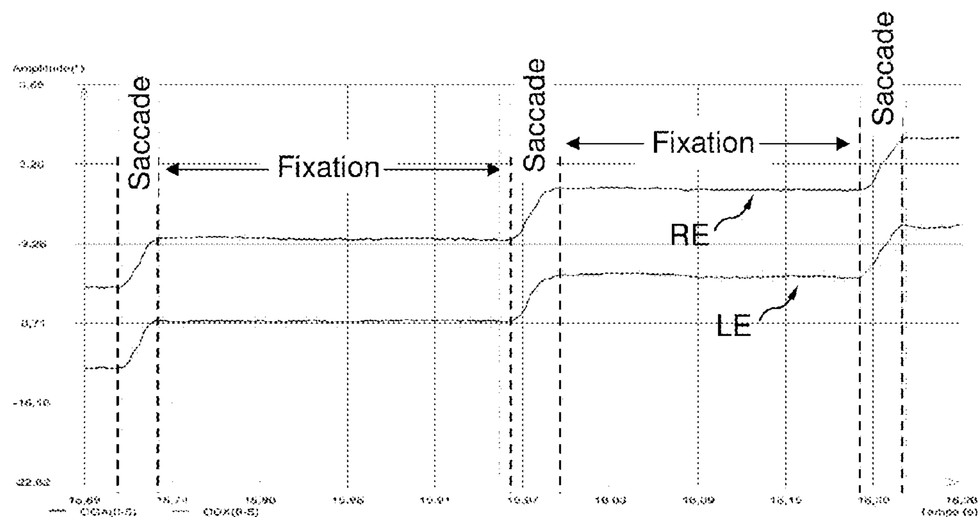
FIG. 5 shows a recording of the movements of the eyes of a healthy subject during a visual search test.

FIG. 5 shows a portion of the recordings for the right eye RE (upper curve) and for the left eye LE (lower curve), in a subject without dyslexia, during the visual search test.

The acquisition and processing part of system 1 also comprises a digital processing module 17 configured for determining the value of at least one parameter of binocular coordination 18 from the recordings 16.

This module 17 in particular identifies saccades and post-saccadic fixations on the recordings 16. As described in the work of C. Prado et al., a saccade can be identified at the places where the movements of the eye present a peak in velocity greater than 30°/s and less than 800°/s and an amplitude of displacement greater than 1 degree relative to the position of fixation before the saccade is triggered. The start and finish of the saccade can be delimited by the change of sign of the velocity on two rear points. Of course, other criteria can be employed, in particular, for example, an algorithm where the threshold of detection of the velocity is dynamic, i.e. averaged per subject in general for a signal duration of less than 20 seconds. The velocity is then preferably calculated at 3 centred points.

For the example in FIG. 5, a saccade is thus identified around the time point 15.97 s, representing a significant displacement of the eyes of about 3 to 4 degrees (transition zone between two horizontal plateaux).

By definition, the post-saccadic fixations correspond to the periods between two saccades, i.e. the horizontal plateaux in FIG. 5.

The processing module 17 in particular determines several parameters of binocular coordination as described hereafter.

Finally, the acquisition and processing part of system 1 comprises a module 19 for comparing the value determined of the parameter 18 with at least one threshold value VS so as to determine an oculomotor abnormality.

This module can consist for example of producing an oculomotor report 20 on which the various parameters determined by module 17 appear, as well as the corresponding threshold values.

As a variant, this module can perform a numerical comparison between the value of the parameters considered and their corresponding threshold values to produce decision information of the type "dyslexic subject" or "non-dyslexic subject".

Figure 6:
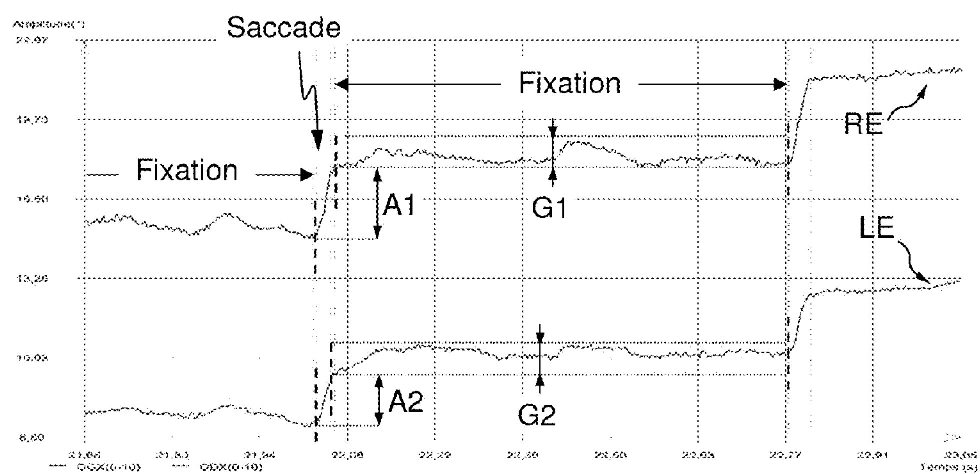
FIG. 6 shows a recording of the movements of the eyes of a dyslexic subject during a visual search test.

FIG. 6 shows a portion of the recordings for the right eye RE (upper curve) and for the left eye LE (lower curve) in a subject with dyslexia, during the visual search test mentioned previously (FIG. 2).

Module 17 in particular determines the following parameters:

- conjugacy during saccades in amplitude, designated $C_{Sacc}$,
- disconjugacy during saccades in amplitude, designated $D_{Sacc}$,
- disconjugacy of post-saccadic fixation period in amplitude, designated $D_{Fix}$,
- conjugacy of post-saccadic fixation period in amplitude, designated $C_{Fix}$,
- duration of post-saccadic fixation period, designated $T_{Fix}$.

These parameters are in particular average values obtained for all of the saccades and post-saccadic fixations during the test.

Now, how these parameters were obtained will be described for one occurrence of saccade or of fixation, it being understood that all of the values obtained are subsequently averaged.

Regarding conjugacy during saccades in amplitude $C_{Sacc}$, the module 17 determines the amplitude A1 in degrees of displacement of the right eye and the amplitude A2 for the left eye.

This amplitude can be calculated as the difference between the amplitude at end of saccade and the amplitude at start of saccade. As a variant, it can be the difference between the maximum amplitude and the minimum amplitude during the saccade.

The conjugacy during saccades in amplitude then corresponds to (A1+A2)/2.

The disconjugacy during saccades in amplitude $D_{Sacc}$ is obtained from A2−A1. It therefore represents a difference in movement between the two eyes during the displacement of the eyes from one letter or group of letters to another.

As a variant, this disconjugacy during saccades can be obtained by averaging the absolute difference between the two curves, subtracting from this average the initial difference at the start of the saccade (corresponding to superposing the two curves at their initial point of the start of saccade), if the durations of the two saccades RE and LE are approximately concomitant.

The conjugacy $C_{Fix}$ and the disconjugacy $D_{Fix}$ of post-saccadic fixation period are obtained similarly for the next fixation phase: G1 is the amplitude in degrees of the displacement of the right eye during fixation (either between the initial and final positions, or between the minimum and maximum positions as shown on the figure), G2 similarly for the left eye. Thus: $C_{Fix}$=(G1+G2)/2 and $D_{Fix}$=G2−G1.

As for the duration of post-saccadic fixation $T_{Fix}$, it is the average between the duration of the post-saccadic fixation of the right eye and the duration of the post-saccadic fixation of the left eye.

The results of visual search tests carried out on 19 dyslexic children and 50 children reading normally, from 7 to 15 years of age, tested as a function of their age (FIGS. 5 to 9), will now be described.

The children reading normally in particular made it possible to establish normal values and threshold values corresponding to $p<0.05$ (i.e. 5% equivalent to twice the standard deviation from the mean) for the parameters mentioned above. The invention is not, however, limited to this type of thresholding, and other techniques can be employed for improving or relaxing the constraints on the presence of false positives.

The children are distributed in three age groups: 7-9 years, 10-12 years and 13-15 years.

For the children in the 7-9 years group, the visual search task for the letter "r" is carried out on the paragraph in FIG. 2. For the other groups, the paragraph in FIG. 3 was used.

The eye movements were recorded by the Mobile EBT® video-oculography system.

The 7-9 years group comprised seventeen healthy subjects (i.e. not dyslexic) serving as controls for establishing the normal values of the aforementioned parameters, as well as the corresponding threshold values ($p<0.05$), in particular the upper limits.

Five dyslexic subjects, designated D1 to D5, were then tested.

The table in FIG. 7 shows the results obtained, in which the numbers in bold and underlined on a grey background exceed a threshold value of detection. The first column records the subjects (D1 to D5 for the dyslexic subjects, ND1 to ND4 for four of the healthy subjects), and the other columns give the parameters $C_{Sacc}$, $D_{Sacc}$, $D_{Fix}$, $C_{Fix}$ and $T_{Fix}$, respectively.

This table shows, similarly to the results already known for this visual search test (for example the work of C. Prado et al.), that the amplitude of the saccades $C_{Sacc}$ does not have a significant difference between the dyslexic subjects and the healthy subjects ($p=0.64$).

On the other hand, a disorder of binocular coordination is stressed for the dyslexic subjects with:

- a disconjugacy during saccades $D_{Sacc}$ that is greater for the dyslexic subjects D1 to D5 than for the healthy subjects [$p<0.003$];
- a conjugacy of fixation period $C_{Fix}$ that is greater for the dyslexic subjects D1 to D5 than for the healthy subjects [$p<0.002$];
- a disconjugacy of post-saccadic fixation period $D_{Fix}$ that is greater for the dyslexic subjects D1 to D5 than for the healthy subjects [$p<0.001$]; and
- a duration of fixation period $T_{Fix}$ that is greater for the dyslexic subjects D1 to D5 than for the healthy subjects [$p<0.001$].

It should be noted, moreover, that just one of the parameters of disconjugacy $D_{Sacc}$ and $D_{Fix}$ or the two taken in isolation make it possible to detect dyslexic subjects relatively reliably. In fact, their values are generally substantially higher than the normal range of the healthy subjects.

The 10-12 years group comprised seventeen healthy subjects and eleven dyslexic subjects, designated D1 to D11.

The table in FIG. 8 shows the results obtained, in the same format as for FIG. 7.

As in the case of the 7-9 years group, the amplitude of the saccades $C_{Sacc}$ does not display a significant difference between the dyslexic subjects and the healthy subjects ($F<1$; $p=0.59$).

On the other hand, a disorder of binocular coordination is observed for the dyslexic subjects with:

- a disconjugacy during saccades $D_{Sacc}$ that is greater for the dyslexic subjects D1 to D11 than for the healthy subjects [$F(1.26)=30.4$, $p<0.001$].
- a conjugacy of fixation period $C_{Fix}$ that is greater for the dyslexic subjects D1 to D11 than for the healthy subjects [$F(1.26)=19.1$, $p<0.001$].
- a disconjugacy of post-saccadic fixation period $D_{Fix}$ that is greater for the dyslexic subjects D1 to D11 than for the healthy subjects [$F(1.26)=29.8$, $p<0.001$].
- a duration of fixation period $T_{Fix}$ that is greater for the dyslexic subjects D1 to D11 than for the healthy subjects [$F(1.26)=5.1$, $p<0.03$].

Similarly to the 7-9 years group, by combining these four parameters it is possible to identify the dyslexic subjects without ambiguity. It should be noted that the only parameter of disconjugacy of post-saccadic fixation period $D_{Fix}$ also allows these dyslexic subjects to be identified.

Finally, the 13-15 years group comprised sixteen healthy subjects and three dyslexic subjects, designated D1 to D3.

The table in FIG. 9 gives the results obtained in the same format as for the two preceding figures.

A slight difference is observed in the amplitude of the saccades $C_{Sacc}$ between the dyslexic subjects and the healthy subjects ($p<0.02$) in particular with a greater variability for the dyslexics.

As for the other two groups, a disorder of binocular coordination is observed for the dyslexic subjects on the basis of the four parameters already mentioned:

- a disconjugacy during saccades $D_{Sacc}$ that is greater for the dyslexic subjects D1 to D3 than for the healthy subjects [$p<0.03$].
- a conjugacy of fixation period $C_{Fix}$ that is greater for the dyslexic subjects D1 to D3 than for the healthy subjects [$p<0.001$].
- a disconjugacy of post-saccadic fixation period $D_{Fix}$ that is greater for the dyslexic subjects D1 to D3 than for the healthy subjects [$p<0.02$].
- a duration of fixation period $T_{Fix}$ that is greater for the dyslexic subjects D1 to D3 than for the healthy subjects [$p<0.001$].

The present invention makes it possible, by using particular parameters of binocular coordination, to identify subjects suffering from an oculomotor abnormality by a simple visual search test that does not require the ability to read. It is therefore favourable for detecting dyslexia in very young children.

The preceding examples are just some embodiments of the invention, which is not limited to these.

The invention claimed is:

1. A test method for establishing a parameter of binocular coordination in a subject, comprising:

subjecting the subject to a visual search task for occurrences of a symbol within a succession of symbols;

during said visual search task, recording the movements of the subject's two eyes using a device for tracking eye movements; then determining, using a digital processing device, the value of at least one parameter of binocular coordination from the recordings obtained.

2. The method according to claim 1, in which at least one parameter of binocular coordination comprises at least one parameter of binocular disconjugacy in amplitude.

3. The method according to claim 2, in which at least one parameter of binocular disconjugacy comprises a parameter of disconjugacy during saccades representative of a difference in movement between the two eyes during displacement of said eyes from one symbol to another.

4. The method according to claim 2, in which at least one parameter of binocular disconjugacy comprises a parameter of disconjugacy of post-saccadic fixation period representative of a difference in movement between the two eyes during fixation of a symbol.

5. The method according to claim 1, in which determination of the value of at least one parameter of binocular coordination comprises identification, by the digital processing device, of saccades and of post-saccadic fixations on the recordings, and comprises calculation of the at least one parameter of binocular coordination as a function of the saccades and post-saccadic fixations identified.

6. The method according to claim 5, in which at least one parameter of binocular coordination is representative of an average of several saccades or several post-saccadic fixations.

7. The method according to claim 6, in which determination of at least one parameter of binocular conjugacy in amplitude from the recordings includes comparison of the parameter of conjugacy with at least one threshold value.

8. The method according to claim 7, in which the following parameters are determined from the recordings and compared with threshold values:

a parameter of disconjugacy during saccades in amplitude, a parameter of disconjugacy of post-saccadic fixation period in amplitude, a parameter of conjugacy of post-saccadic fixation period in amplitude, a duration of post-saccadic fixation period.

9. A system for assisting the detection of an oculomotor abnormality in a subject, comprising:

a testing module for subjecting the subject to a visual search task for occurrences of a symbol within a succession of symbols;

a module for tracking eye movements configured for recording, during said visual search task, the movements of the subject's two eyes;

a digital processing module configured for determining the value of at least one parameter of binocular coordination from the recordings;

a module for comparing the value determined with at least one threshold value so as to determine an oculomotor abnormality.

10. A method for diagnosing an oculomotor disorder, comprising:

providing a system as recited in claim 9;

subjecting the subject to a visual search task for occurrences of a symbol within a succession of symbols;

recording, during said visual search task, the movements of the subject's two eyes;

determining the value of at least one parameter of binocular coordination from the recordings;

comparing the value determined with at least one threshold value so as to determine an oculomotor abnormality.

11. The method according to claim 3, in which at least one parameter of binocular disconjugacy comprises a parameter of disconjugacy of post-saccadic fixation period representative of a difference in movement between the two eyes during fixation of a symbol.

12. The system according to claim 9, wherein at least one parameter of binocular coordination comprises at least one parameter of binocular disconjugacy in amplitude.

13. The system according to claim 12, wherein at least one parameter of binocular disconjugacy comprises a parameter of disconjugacy during saccades representative of a difference in movement between the two eyes during displacement of said eyes from one symbol to another.

14. The system according to claim 12, wherein at least one parameter of binocular disconjugacy comprises a parameter of disconjugacy of post-saccadic fixation period representative of a difference in movement between the two eyes during fixation of a symbol.

15. The system according to claim 9, wherein determination of the value of at least one parameter of binocular coordination comprises identification, by the digital processing device, of saccades and of post-saccadic fixations on the recordings, and comprises calculation of the at least one parameter of binocular coordination as a function of the saccades and post-saccadic fixations identified.

16. The system according to claim 15, wherein at least one parameter of binocular coordination is representative of an average of several saccades or several post-saccadic fixations.

17. The system according to claim 16, wherein determination of at least one parameter of binocular conjugacy in amplitude from the recordings includes comparison of the parameter of conjugacy with at least one threshold value.

18. The system according to claim 17, wherein the following parameters are determined from the recordings and compared with threshold values:

a parameter of disconjugacy during saccades in amplitude, a parameter of disconjugacy of post-saccadic fixation period in amplitude, a parameter of conjugacy of post-saccadic fixation period in amplitude, a duration of post-saccadic fixation period.

* * * * *